(12) United States Patent
Chuang et al.

(10) Patent No.: US 11,739,044 B2
(45) Date of Patent: Aug. 29, 2023

(54) METHOD FOR SYNTHESIZING ARTEPILLIN C AND INTERMEDIATE COMPOUND THEREOF

(71) Applicant: GWO XI STEM CELL APPLIED TECHNOLOGY CO., LTD., Zhubei (TW)

(72) Inventors: Ming-Hsi Chuang, Zhubei (TW); Lin-Hsiang Chuang, Zhubei (TW); Ming-Hsuan Lu, Zhubei (TW); Wen-Peng Shen, Zhubei (TW); Yun-Chen Lin, Zhubei (TW); Chi-Hsuan Chuang, Zhubei (TW)

(73) Assignee: GWO XI STEM CELL APPLIED TECHNOLOGY CO., LTD., Zhubei (TW)

(*) Notice: Subject to any disclaimer, the term of this patent is extended or adjusted under 35 U.S.C. 154(b) by 0 days.

(21) Appl. No.: 17/183,324

(22) Filed: Feb. 23, 2021

(65) Prior Publication Data

US 2022/0098139 A1 Mar. 31, 2022

(30) Foreign Application Priority Data

Sep. 25, 2020 (TW) .................................. 109133304

(51) Int. Cl.
*C07C 51/09* (2006.01)
*C07C 51/42* (2006.01)
*C07C 59/52* (2006.01)

(52) U.S. Cl.
CPC .............. *C07C 51/09* (2013.01); *C07C 51/42* (2013.01); *C07C 59/52* (2013.01)

(58) Field of Classification Search
None
See application file for complete search history.

(56) References Cited

PUBLICATIONS

Patra et al. (Angewandte Chemie, 2016, 55(27), 7751). (Year: 2016).*

(Continued)

*Primary Examiner* — Sudhakar Katakam
*Assistant Examiner* — Jennifer C Sawyer

(57) ABSTRACT

The present invention relates to a method for synthesizing artepillin C and a synthetic method for synthesizing an intermediate compound for use in preparing artepillin C. The structural formula of artepillin C is shown in the following formula (IV), and the intermediate compound is shown in the following formula (II). The synthesis method includes the following steps: a first reaction step: in the presence of a base initiator, a compound A shown in formula I and 3,3-dimethylallyl bromide are mixed, the reaction continues for a first reaction time and is stopped to generate an intermediate of artepillin C shown in formula II; and a second reaction step: the intermediate of artepillin C is dissolved in an aqueous alcohol solution and then mixed with an alkali metal salt, and the reaction continues for a second reaction time to generate artepillin C.

(I)

(II)

(Continued)

-continued
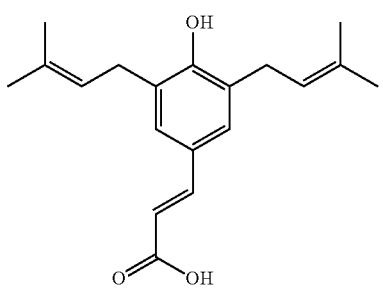
(IV)
10 Claims, 1 Drawing Sheet
(56) References Cited
PUBLICATIONS
Supporting Information for Patra et al. (Angewandte Chemie, 2016, 55(27), 7751). (Year: 2016).*
* cited by examiner

```
┌─────────────────────────────────────────────┐
│ First reaction step: in the presence of a base │
│ initiator, a compound A and 3,3-dimethylallyl │
│ bromide are mixed, and the reaction continues │ ─ S1
│ for a first reaction time and is stopped to   │
│ generate a first reaction product, which      │
│ includes an intermediate of artepillin C and a│
│ compound C                                    │
└─────────────────────────────────────────────┘
                      │
                      ▼
┌─────────────────────────────────────────────┐
│ First purification step: in an acidic       │
│ environment, the first reaction product is  │
│ extracted with ethyl acetate to obtain a    │ ─ S11
│ first crude extract, and then the first     │
│ crude extract is purified by normal phase   │
│ column chromatography to obtain the         │
│ purified intermediate of artepillin C       │
└─────────────────────────────────────────────┘
                      │
                      ▼
┌─────────────────────────────────────────────┐
│ Second reaction step: the intermediate of   │
│ artepillin C is dissolved in an aqueous     │
│ alcohol solution and then mixed with an     │ ─ S2
│ alkali metal salt, and the reaction         │
│ continues for a second reaction time to     │
│ generate a second reaction product, which   │
│ includes artepillin C                       │
└─────────────────────────────────────────────┘
                      │
                      ▼
┌─────────────────────────────────────────────┐
│ Second purification step: in an acidic      │
│ environment, the second reaction product is │
│ extracted with ethyl acetate to obtain a    │ ─ S21
│ second crude extract, and then the second   │
│ crude extract is purified by normal phase   │
│ column chromatography to obtain purified    │
│ artepillin C                                │
└─────────────────────────────────────────────┘
```

METHOD FOR SYNTHESIZING ARTEPILLIN C AND INTERMEDIATE COMPOUND THEREOF

CROSS-REFERENCE TO RELATED APPLICATIONS

This application claims the benefit of Taiwanese Patent Application No. 109133304, filed on Sep. 25, 2020, the contents of which are incorporated herein by reference in their entireties.

BACKGROUND OF THE INVENTION

1. Field of the Invention

The present invention relates to methods for preparing drugs, and more particularly to a method for synthesizing artepillin C and a method for synthesizing an intermediate thereof.

2. Description of the Related Art

Propolis has anti-oxidation and anti-cancer effects. At present, many studies and papers have found or confirmed that propolis can effectively shrink tumors, kill cancer cells, inhibit the growth and metastasis of malignant tumors, reduce adverse reactions of chemotherapy, enhance anti-cancer immunity, and improve fibrosis, and the like. This is because propolis contains flavonoids, artepillin C, enzymes and organic acids and other components, which have the function of inhibiting and killing cancer cells.

Artepillin C is a unique active ingredient of Brazilian propolis. In recent years, researches on propolis have demonstrated the role of artepillin C in the repair of cancer cells and nerves. It not only inhibits the proliferation and migration of cancer cells and promotes apoptosis of cancer cells, but also has antioxidant properties and helps neural synapse growth. Thus, artepillin C is considered as a candidate ingredient for future development of medicines in the fields of cancer medicine and nerve regeneration.

The method of extracting artepillin C from Brazilian propolis has been developed for many years. For example, in European Patent EP0976399B1, crushed propolis mass is soaked in ethanol, glycerin and/or water to obtain an available propolis extract, and then flavonoids and artepillin C in the extract are treated with an anion exchange resin. However, the process of removing waxy components in propolis by organic solvent treatment in this method that will cause serious loss of artepillin C and flavonoids. Further, in Chinese Patent CN1108057A, propolis is soaked in glycerin, heated, stirred and filtered while hot to prepare a water-soluble propolis. However, this method cannot remove waxy components in propolis, and the co-solvent will greatly reduce the purity of artepillin C and flavonoids in propolis, so that propolis cannot effectively exert its functions. It can be seen that the conventional methods of obtaining artepillin C by extraction all have the problem that the purity cannot be improved. Moreover, as the export volume of Brazilian propolis decreases year by year, the difficulty of obtaining artepillin C from Brazilian propolis by extraction has also increased.

Therefore, the industry has begun to prepare the active ingredient in propolis, artepillin C, through a fully synthetic method, so as to overcome the problems of insufficient purity and year-by-year declining raw materials for propolis and make it easier to control quality. However, the current synthesis process of artepillin C has the problems of expensive initiators, high toxicity of reaction solvents, cumbersome steps, time-consuming reaction, and low final yield, so that it is only suitable for milligram-level quantities and is difficult to be used in mass production and commercial sales.

Therefore, there is an urgent need in various industries to develop a new synthesis method that can overcome the above-mentioned problems and can facilitate mass production.

SUMMARY OF THE INVENTION

Therefore, in view of these, the present inventors have discussed various possible solutions to the problems of the above-mentioned conventional technologies, and have discovered a novel synthesis method of artepillin C through a large number of analysis, experiments and researches. The synthesis method can effectively solve the technical problems and shortcomings of the existing technologies, and not only simplifies the synthesis steps, but also can be used in mass production and commercial sales.

That is, an object of the present invention is to provide a method for synthesizing artepillin C, which includes the following steps: a first reaction step: in the presence of a base initiator, a compound A shown in formula I and 3,3-dimethylallyl bromide are mixed, and the reaction continues for a first reaction time and is stopped to generate a first reaction product, which includes an intermediate of artepillin C shown in formula II;

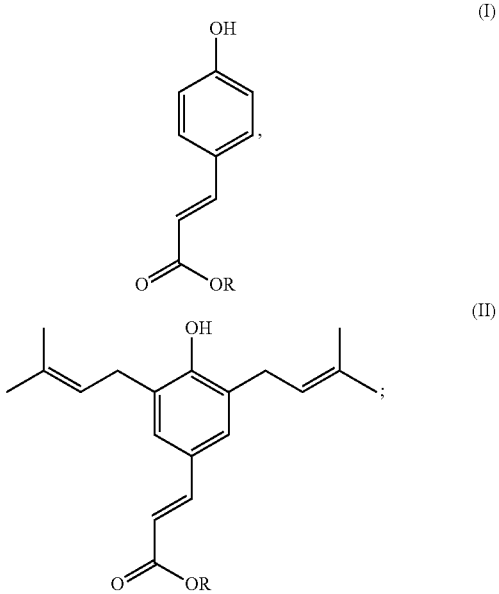

in which R is $C_{1-6}$ alkyl; and a second reaction step: the intermediate of artepillin C is dissolved in an aqueous alcohol solution and then mixed with an alkali metal salt, and the reaction continues for a second reaction time to generate a second reaction product, which includes artepillin C shown in formula IV;

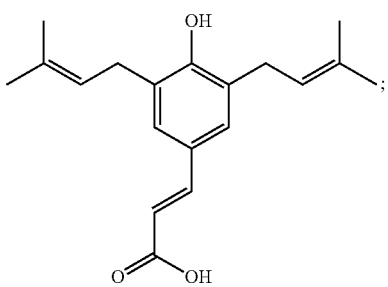

(IV)

wherein in the first reaction step, the reaction of the compound A with 3,3-dimethylallyl bromide is carried out in toluene, dimethylformamide, tetrahydrofuran, or dimethylsulfoxide, and the first reaction time is between 72 h and 120 h; and in the second reaction step, the second reaction time is between 8 h and 20 h.

According to a specific embodiment of the present invention, the base initiator is sodium hydride.

According to a specific embodiment of the present invention, the first reaction step is carried out in an ice bath environment.

According to a specific embodiment of the present invention, after the first reaction step, a first purification step is further included: in an acidic environment, the first reaction product is extracted with ethyl acetate to obtain a first crude extract, and then the first crude extract is purified by normal phase column chromatography to obtain a purified intermediate of artepillin C.

According to a specific embodiment of the present invention, after the second reaction step, a second purification step is further included: in an acidic environment, the second reaction product is extracted with ethyl acetate to obtain a second crude extract, and then the second crude extract is purified by normal phase column chromatography to obtain purified artepillin C.

According to a specific embodiment of the present invention, the acidic environment has a pH value between 1 and 5.

Further, another object of the present invention is to provide a method for synthesizing an intermediate for use in preparing artepillin C, which includes the following steps: in the presence of a base initiator, a compound A shown in formula I and 3,3-dimethylallyl bromide are mixed, and the reaction continues for a first reaction time and is stopped to generate a first reaction product, which includes an intermediate of artepillin C shown in formula II;

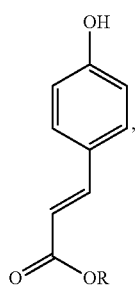

(I)

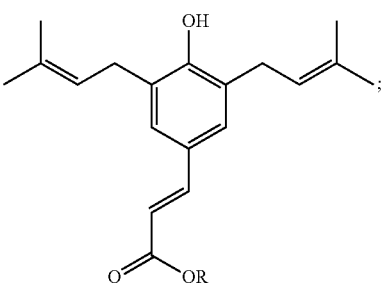

(II)

in which R is $C_{1-6}$ alkyl.

BRIEF DESCRIPTION OF THE DRAWINGS

The sole FIGURE is a flow chart showing the steps of the synthesis method of the present invention.

DETAILED DESCRIPTION OF THE PREFERRED EMBODIMENTS

In order to enable those skilled in the art to better understand the objects, technical features, and advantages of the present invention and accordingly implement the present invention, the technical features and implementations of the present invention are illustrated in detail herein in conjunction with the accompanying drawings, and preferred embodiments are exemplified for further description. The drawings referenced in the following description are schematic representations for expressing the features of the present invention, and are not and need not be drawn completely based on actual situations.

The singular forms "a/an", "one" and "the" used herein also include plural forms, unless the context clearly indicates otherwise. Furthermore, it should be understood that when used in this specification, the terms "including" and/or "comprising" designate the presence of features, elements and/or units described, but do not exclude the presence or addition of one or more other features, elements and/units. Also, in the following detailed description of each embodiment with reference to the drawings, it will be clearly presented that the directional terms mentioned in the following embodiments, for example: "upper", "lower", "left", "right", "front", "rear", etc., are only used to designate directions in the drawings to which reference is made. Therefore, the directional terms are intended to be used for explanation, but not to limit the present invention.

Although numerical ranges and parameters used to define a wider range of the present invention all are approximate numerical values, relevant numerical values in the specific embodiments are presented herein as accurately as possible. However, any value inherently inevitably contains standard deviations due to individual test methods. Herein, "about" usually means that an actual value is within plus or minus 10%, 5%, 1% or 0.5% of a specific value or range. Or, the word "about" means that an actual value falls within an acceptable standard error of a mean value, depending on the consideration of those having ordinary skill in the art of the present invention. Except experimental examples, or unless otherwise clearly stated, all ranges, amounts, values and percentages used herein (for example, used to describe the amount of materials, length of time, temperature, operating conditions, amount ratio and the like) should be understood to be modified by "about". Therefore, unless otherwise stated to the contrary, numerical parameters disclosed in this specification and the accompanying claims all are approximate values and can be varied according to requirements. At least these numerical parameters should be understood as indicated effective digits and numerical values obtained by applying the general carry method.

In order to make the description of the present disclosure more exhaustive and complete, the following provides an illustrative description for the implementation aspects and specific embodiments of the present invention; but this is not the only way to implement or use the specific embodiments of the present invention. The implementations cover the features of a number of specific embodiments, and the method steps and sequences used to construct and operate these specific embodiments. However, other specific embodiments can also be used to achieve the same or equal functions and sequence of steps.

First of all, the synthesis method of the present invention will be explained in conjunction with FIG. 1 and the following reaction scheme:

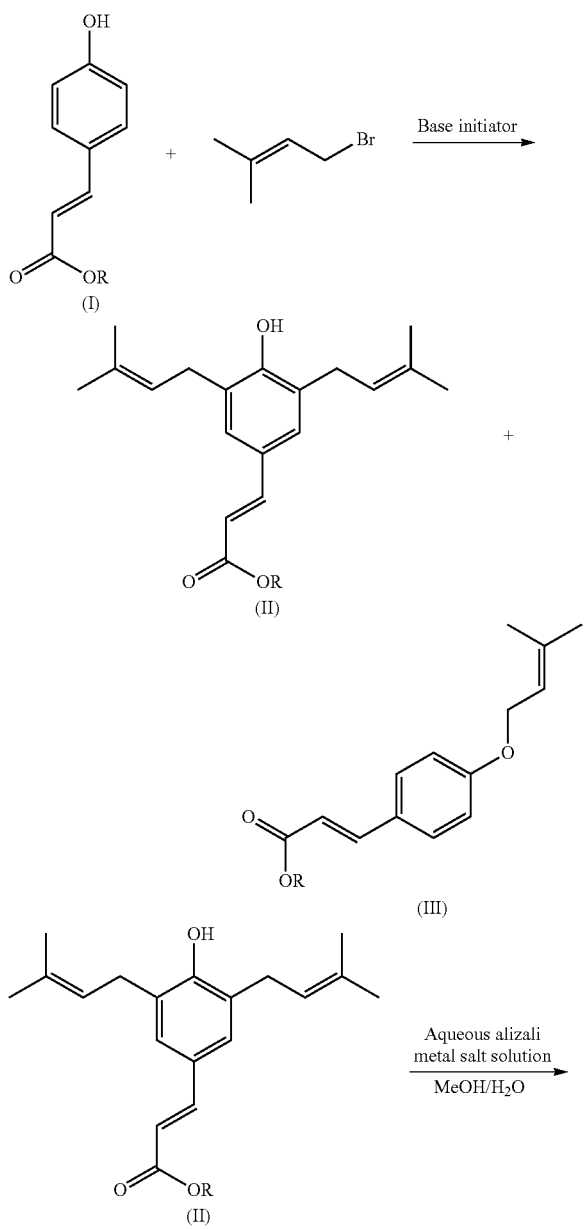

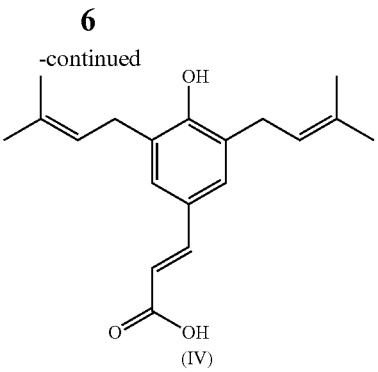

As shown in the sole FIGURE, the synthesis method of the present invention includes the following steps:

a first reaction step S1: in the presence of a base initiator, a compound A shown in formula I and 3,3-dimethylallyl bromide are mixed, and the reaction continues for a first reaction time and is stopped to generate a first reaction product, which includes an intermediate of artepillin C shown in formula II and a compound C shown in formula III.

a second reaction step S2: the intermediate of artepillin C is dissolved in an aqueous alcohol solution and then mixed with an alkali metal salt, and the reaction continues for a second reaction time to generate a second reaction product, which includes artepillin C shown in formula IV.

According to the technical idea of the present invention, in formula I and formula II, R is a branched or straight chain alkyl group having 1 to 6 carbon atoms ($C_{1-6}$ alkyl), and for example, may be any one selected from the group consisting of methyl, ethyl, n-propyl, isopropyl, n-butyl, sec-butyl, tert-butyl, n-pentyl, and n-hexyl; preferably any one selected from the group consisting of methyl, ethyl, n-propyl, isopropyl, and n-butyl; more preferably any one selected from the group consisting of methyl, ethyl, and n-propyl; and most preferably methyl or ethyl. In addition, the base initiator is generally sodium hydride (NaH).

In the first reaction step, the molar ratio of the compound A to 3,3-dimethylallyl bromide is between 1:0.5 and 1:2.5, preferably between 1:1 and 1:2.5, more preferably between 1:1.5 and 1:2.5, and most preferably 1:2; and the molar ratio of the compound A to the base initiator is between 1:0.5 and 1:2.5, preferably between 1:1 and 1:2.5, more preferably between 1:1.5 and 1:2, and most preferably 1:2. In addition, the first reaction step is carried out in an organic solvent, and the organic solvent may be any one selected from toluene, dimethylformamide (DMF), tetrahydrofuran (THF), and dimethylsulfoxide (DMSO). Furthermore, in order to prevent the base initiator from reacting with air, the first reaction step is preferably carried out in an ice bath environment.

Accordingly, the first reaction time depends on whether the reactants are completely reacted, which can be confirmed by thin layer chromatography (TLC). In an embodiment of the present invention, the first reaction time is generally between 72 h and 120 h, preferably between 72 h and 110 h, more preferably between 72 h and 100 h, and most preferably between 72 h and 90 h. If the reaction time is too long, the intermediate of artepillin C will be degraded into the compound C, resulting in a decrease in the yield of the intermediate of artepillin C as a reactant in the second reaction step.

According to the creative idea of the present invention, after the first reaction step, a first purification step S11 may be further included: in an acidic environment, the first reaction product is extracted with ethyl acetate to obtain a first crude extract, and then the first crude extract is purified by normal phase column chromatography to obtain the purified intermediate of artepillin C, artepillin C methyl ester (3-(4-hydroxy-3,5-bis(3-methyl-2-butenyl)phenyl)acrylic acid methyl ester). The product yield of the purified intermediate of artepillin C is above 35%, and more preferably above 40%; in addition, the purity of the intermediate of artepillin C is above 95%, and most preferably above 98%.

Furthermore, in the second reaction step, the intermediate of artepillin C is dissolved in an aqueous alcohol solution and then mixed with an aqueous alkali metal salt solution for reaction to obtain artepillin C. In an embodiment of the present invention, the intermediate of artepillin C purified by the first purification step is dissolved in an aqueous alcohol solution. The molar concentration of the intermediate of artepillin C in the aqueous alcohol solution is between 0.5M and 5.0M, preferably between 1.0M and 4.0M, more preferably between 2.0M and 3.5M, and most preferably between 2.5M and 3.0M. The molar concentration of the aqueous alkali metal salt solution is between 5M and 10.0 M, preferably between 5.5M and 9.0M, more preferably between 6.0M and 7.0M, and most preferably between 6.0M and 6.5M. The volume ratio of the aqueous alcohol solution to the aqueous alkali metal salt solution is 5:1, preferably 2.44:1, more preferably 1.51:1, and most preferably 1.12:1.

In addition, according to the creative idea of the present invention, the aqueous alcohol solution is an aqueous methanol solution with a concentration of 50 vt %, but it is not limited thereto.

Like the first reaction time, the second reaction time also depends on whether the reactants are completely reacted, which can be confirmed by thin layer chromatography (TLC). In an embodiment of the present invention, the second reaction time is generally between 8 h and 20 h, preferably between 10 h and 15 h, and most preferably between 12 h and 15 h.

According to the creative idea of the present invention, after the second reaction step, a second purification step S21 is further included: in an acidic environment, the second reaction mixture is extracted with ethyl acetate to obtain a second crude extract, and then the second crude extract is purified by normal phase column chromatography to obtain purified artepillin C. The product yield of purified artepillin C is above 35%, preferably between 35% and 50%, and more preferably between 40% and 50%, and the purity of artepillin C is above 95%, and most preferably above 98%.

Next, the present invention will be explained with specific examples below.

Example 1 (First Reaction Step)

Firstly, 9.0 g (51.0 mmol) of methyl 4-hydroxycinnamate and 150 ml of toluene were weighed into a conical flask respectively, and stirred uniformly with a magnetic stirrer to completely dissolve methyl 4-hydroxycinnamate in toluene. Then, the conical flask was placed in an ice bath, and 4.4 g (110.0 mmol) of sodium hydride was slowly added while constantly stirring until sodium hydride was completely dissolved. After that, 16.0 g (107.0 mmol) of 3,3-dimethylallyl bromide was added. Then, the conical flask was evacuated to remove oxygen and charged with argon gas. The reaction was carried out in argon gas in the ice bath environment.

After 72 h of reaction, a TLC plate (developing solvent: n-hexane:ethyl acetate=10:1) was used to confirm that the reaction starting materials had been completely reacted, and 50 ml of water was slowly poured into the reaction solution to stop the reaction. Next, dilute hydrochloric acid was added to adjust the pH of the reaction solution to be between 1 and 5. Then, the reaction solution was extracted with 250 ml of ethyl acetate. An organic layer was removed and anhydrous magnesium sulfate was added to the organic layer to remove water, and then ethyl acetate was removed by vacuum concentration, to obtain a crude extract.

The crude extract was purified by normal phase column chromatography (stationary phase: silica gel; mobile phase: n-hexane/ethyl acetate, gradient 20:1 to 10:1) to obtain an intermediate of artepillin C (artepillin C methyl ester (3-(4-hydroxy-3,5-bis(3-methyl-2-butenyl)phenyl)acrylic acid methyl ester), with a product yield of 45%) and a by-product compound C (with a product yield of 25%). The structure and purity of the intermediate of artepillin C (artepillin C methyl ester) and the compound C were confirmed with a nuclear magnetic resonance spectrometer. The NMR spectrum data of the intermediate of artepillin C is: $^1$H-NMR (400 MHz, $CDCl_3$) δ 7.60 (d, J=16.0 Hz, 1H), 7.17 (s, 2H), 6.28 (d, J=16.0 Hz, 1H), 5.66 (s, 1H), 5.31 (t, J=6.83 Hz, 2H), 3.79 (s, 3H), 3.34 (d, J=6.83 Hz, 4H), 1.79 (s, 6H), 1.77 ppm (s, 6H); $^{13}$C-NMR (100 MHz, $CDCl_3$) δ 166.5, 153.6, 143.6, 131.8, 128.0, 127.6, 127.0, 123.1, 115.1, 52.0, 28.5, 24.6, 18.6 ppm, with a purity of 98%; and the NMR spectrum data of the compound C is: $^1$H-NMR (400 MHz, $CDCl_3$) δ 7.65 (d, J=16.0 Hz, 1H), 7.46 (d, J=8.8 Hz, 2H), 6.90 (d, J=8.8 Hz, 2H), 6.30 (d, J=16.0 Hz, 1H), 5.48 (t, J=6.6 Hz, 1H), 4.54 (d, J=6.6 Hz, 2H), 3.80 (s, 3H), 1.80 (s, 3H), 1.75 ppm (s, 3H); $^{13}$C-NMR (100 MHz, $CDCl_3$) 167.8, 160.7, 144.6, 138.7, 127.7, 127.0, 119.2, 115.2, 115.0, 64.9, 51.5, 25.8, 18.2 ppm, with a purity of 98%.

Example 2 (Second Reaction Step)

6.0 g (20 mmol) of the intermediate of artepillin C and 7.5 ml of a 50 vt % aqueous methanol solution were placed in a conical flask, and stirred uniformly with a magnetic stirrer to completely dissolve the intermediate of artepillin C in aqueous methanol solution. Then, 7.5 ml of a 6.0M aqueous sodium hydroxide solution was added, and continuously stirred at room temperature for reaction.

After 12 h of reaction, a TLC plate (developing solvent: n-hexane:ethyl acetate=5:1) was used to confirm that the reaction starting materials were completely reacted.

Next, a vacuum concentrator was used to completely remove methanol in the reaction solution, and dilute hydrochloric acid was used to adjust the pH of the reaction solution to be between 1 and 5. Then, the reaction solution was extracted with 100 ml of ethyl acetate. An organic layer was removed and anhydrous magnesium sulfate was added thereto to remove water, and then ethyl acetate was removed by vacuum concentration, to obtain a crude product.

The crude product was purified by normal phase column chromatography (stationary phase: silica gel; mobile phase: n-hexane/ethyl acetate, gradient 20:1 to 5:1) to obtain artepillin C, with a product yield at this stage of 90%, and the total product yield after conversion of about 40.5%. The structure and purity of artepillin C were confirmed with a nuclear magnetic resonance spectrometer. The NMR spectral data of artepillin C is: $^1$H-NMR (400 MHz, $CDCl_3$) δ 7.70 (d, J=15.88 Hz, 1H), 7.20 (s, 2H), 6.29 (d, J=15.84 Hz, 1H), 5.31 (m, 2H), 3.35 (d, J=7.2 Hz, 4H), 1.78 ppm (d, J=6.68 Hz, 12H); $^{13}$C-NMR (100 MHz, $CDCl_3$) δ 172.8, 155.4, 147.4, 135.2, 128.4, 127.7, 126.4, 121.3, 114.1, 29.5, 25.8, 17.9 ppm, with a purity of 98%.

It can be seen from the above-mentioned examples that the present invention provides a simple and efficient method for synthesizing artepillin C, which solves the problems of expensive initiators, high toxicity of reaction solvents, cumbersome steps, time-consuming reaction, and low final yield in the conventional processes for synthesizing artepillin C. This method only requires two synthesis steps, and can be scaled up to gram-level reactions, and a large amount of high-purity artepillin C can be obtained in a short time.

To sum up, the content of the present invention has been specifically described by means of examples in the above embodiments; however, the present invention is not limited to these embodiments. It should be appreciated by those ordinarily skilled in the art that various variations and modifications can be made without departing from the spirit and scope of the invention; for example, all technical contents illustrated in the above embodiments may be combined or changed into a new embodiment, and such embodiments are intended to fall within the scope of the invention. Thus, the scope of the application includes the scope defined in the appended claims.

What is claimed is:

1. A method for synthesizing artepillin C, which comprises the following steps:
   a first reaction step: in the presence of a base initiator, a compound A shown in formula I and 3,3-dimethylallyl bromide are mixed in a solvent including at least one selected from toluene, dimethylformamide, tetrahydrofuran, and dimethylsulfoxide to lead a first reaction in an ice bath continuously for 72 hrs, and then water is poured into the reaction solution to stop the reaction to generate a first reaction product, which comprises an intermediate of artepillin C shown in formula II,

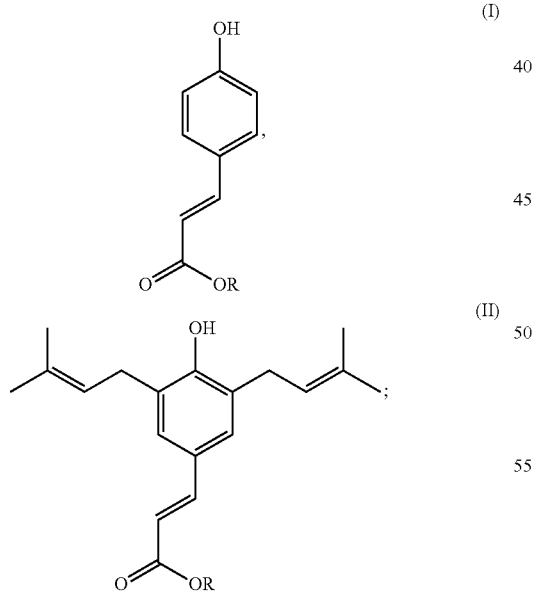

in which R is $C_{1-6}$ alkyl, and
   a second reaction step: the intermediate of artepillin C is dissolved in an aqueous alcohol solution and then mixed with an alkali metal salt, and the reaction continues for a second reaction time to generate a second reaction product, which comprises artepillin C shown in formula IV;

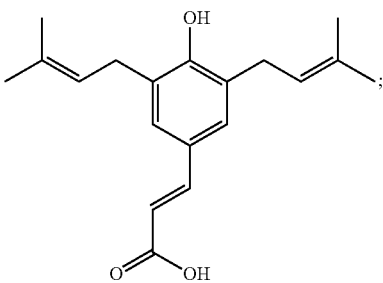

wherein
   in the first reaction step, the molar ratio of the compound A to 3,3-dimethylallyl bromide is 1:2, the molar ratio of the compound A to the base initiator is 1:2, and the first reaction is carried out in a vacuum environment with argon; and
   in the second reaction step, the second reaction time is in the range of 8 h to 20 h.

2. The method for synthesizing artepillin C of claim 1, wherein the base initiator is sodium hydride.

3. The method for synthesizing artepillin C of claim 1, wherein after the first reaction step, a first purification step is further comprised:
   in an acidic environment, the first reaction product is extracted with ethyl acetate to obtain a first crude extract, and then the first crude extract is purified by normal phase column chromatography to obtain the intermediate of artepillin C with a purity of above 95%.

4. The method for synthesizing artepillin C of claim 3, wherein the product yield of the intermediate of artepillin C after purification is above 35%.

5. The method for synthesizing artepillin C of claim 1, wherein after the second reaction step, a second purification step is further comprised:
   in an acidic environment, the second reaction product is extracted with ethyl acetate to obtain a second crude extract, and then the second crude extract is purified by normal phase column chromatography to obtain artepillin C with a purity of above 95%.

6. The method for synthesizing artepillin C of claim 5, wherein the product yield of artepillin C after purification is above 35%.

7. A method for synthesizing an intermediate of artepillin C, which comprises the following steps:
   a reaction step: in the presence of a base initiator, a compound A shown in formula I and 3,3-dimethylallyl bromide are mixed in a solvent including at least one selected from toluene, dimethylformamide, tetrahydrofuran, and dimethylsulfoxide to lead a reaction in an ice bath continuously for 72 hrs, and then water is poured into the reaction solution to stop the reaction to generate an intermediate of artepillin C shown in formula II;

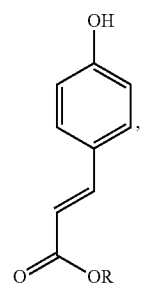

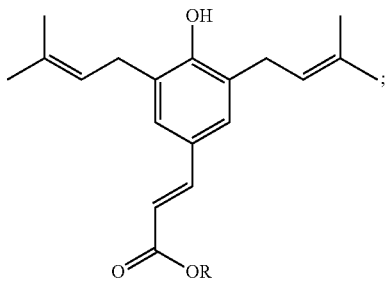

(II)

in which R is $C_{1-6}$ alkyl; wherein the molar ratio of the compound A to 3,3-dimethylallyl bromide is 1:2, the molar ratio of the compound A to the base initiator is 1:2; and the reaction is carried out in a vacuum environment with argon.

8. The method for synthesizing an intermediate of artepillin C of claim 7, wherein after the reaction step, a purification step is further comprised:

in an acidic environment, the reaction mixture obtained by completing the reaction step is extracted with ethyl acetate to obtain a crude extract, and then the crude extract is purified by normal phase column chromatography to obtain the intermediate of artepillin C with a purity of above 95%.

9. The method for synthesizing an intermediate of artepillin C of claim 7, wherein the base initiator is sodium hydride.

10. The method for synthesizing an intermediate of artepillin C of claim 7, wherein the product yield of the intermediate of artepillin C is above 35%.

* * * * *